(12) United States Patent
Wang-Lee

(10) Patent No.: US 9,326,893 B2
(45) Date of Patent: May 3, 2016

(54) GOGGLE STRUCTURE

(71) Applicant: Jiann Lih Optical Co., Ltd., Tainan (TW)

(72) Inventor: Chen-Chang Wang-Lee, Tainan (TW)

(73) Assignee: Jiann Lih OPtical Co., Ltd., Tainan (TW)

( * ) Notice: Subject to any disclaimer, the term of this patent is extended or adjusted under 35 U.S.C. 154(b) by 37 days.

(21) Appl. No.: 14/336,052

(22) Filed: Jul. 21, 2014

(65) Prior Publication Data
US 2015/0290036 A1 Oct. 15, 2015

(30) Foreign Application Priority Data

Apr. 14, 2014 (TW) ................. 10311568 A

(51) Int. Cl.
A61F 9/02 (2006.01)
(52) U.S. Cl.
CPC .................. A61F 9/025 (2013.01); A61F 9/026 (2013.01)
(58) Field of Classification Search
CPC ................................ A61F 9/025; G02C 7/088
USPC ....................................................... 2/426, 439
See application file for complete search history.

(56) References Cited

U.S. PATENT DOCUMENTS

| 2,804,623 | A | * | 9/1957 | Hirschmann | ........... | A61F 9/027 2/445 |
| 2,903,700 | A | * | 9/1959 | Finken | .................... | A61F 9/025 2/10 |
| 3,945,044 | A | * | 3/1976 | McGee | ................... | A61F 9/025 2/434 |
| 4,527,291 | A | * | 7/1985 | Nussbickl | ............... | A61F 9/027 2/450 |
| 4,716,601 | A | * | 1/1988 | McNeal | .................. | A61F 9/025 2/434 |
| 4,977,627 | A | * | 12/1990 | Metcalfe | ................ | G02C 11/08 2/437 |
| 5,018,223 | A | * | 5/1991 | Dawson | ..................... | A61F 9/02 2/436 |
| 5,335,025 | A | * | 8/1994 | Wang | ........................ | G02C 7/10 2/13 |
| 5,363,512 | A | * | 11/1994 | Grabos, Jr. | ............. | G02C 11/08 2/436 |
| 5,376,977 | A | * | 12/1994 | Liu | .......................... | G02C 3/04 351/155 |
| 5,410,763 | A | * | 5/1995 | Bolle | ....................... | A61F 9/025 2/436 |
| 5,412,438 | A | * | 5/1995 | Bolle' | .................... | G02C 5/126 351/138 |
| 5,493,348 | A | * | 2/1996 | Herald, Jr. | ................ | A61F 9/02 2/444 |
| D372,490 | S | * | 8/1996 | Sheffield | ...................... | D16/325 |
| D372,928 | S | * | 8/1996 | Brune | .......................... | D16/311 |
| 5,564,132 | A | * | 10/1996 | Kuo | ......................... | B63C 11/12 2/430 |
| 5,592,698 | A | * | 1/1997 | Woods | ..................... | A42B 3/26 2/424 |
| 5,603,124 | A | * | 2/1997 | Garofalo | ................. | B63C 11/12 2/428 |
| 5,638,552 | A | * | 6/1997 | Fujima | .................... | B63C 11/12 2/428 |
| 5,657,106 | A | * | 8/1997 | Herald, Jr. | ............... | G02C 3/02 2/437 |

(Continued)

Primary Examiner — Richale Quinn
Assistant Examiner — Anne Kozak
(74) Attorney, Agent, or Firm — Alan D. Kamrath; Kamrath IP Lawfirm, P.A.

(57) ABSTRACT

A goggle structure includes a protective soft pad, a frame, and a subsidiary lens frame. Convex portions are formed on upper and lower sides of the subsidiary lens frame and inserted into slots disposed at the frame, respectively. Hook portions are formed on upper and lower sides of the frame and extend backward. By inserting the frame into a receiving space disposed at the protective soft pad, the hook portions press against the periphery of the receiving space. Pressing portions and carrying portions are formed on upper and lower portions at the middle segment of the frame and adapted to hold the protective soft pad. The bottom of the subsidiary lens frame straddles the pressing portions and carrying portions. Branch portions extend from two outer sides of the frame to press against a concave portion of the protective soft pad. Hence, related components are engaged with each other.

3 Claims, 6 Drawing Sheets

(56) References Cited

U.S. PATENT DOCUMENTS

| | | | | |
|---|---|---|---|---|
| 5,689,834 | A * | 11/1997 | Wilson | G02C 11/08 2/435 |
| 5,760,867 | A * | 6/1998 | Pernicka | G02C 1/04 351/118 |
| 5,802,622 | A * | 9/1998 | Baharad | A61F 9/02 2/2.5 |
| 5,867,841 | A * | 2/1999 | Chiang | A61F 9/02 2/436 |
| 6,047,410 | A * | 4/2000 | Dondero | A61F 9/027 2/426 |
| 6,105,177 | A * | 8/2000 | Paulson | A61F 9/027 2/431 |
| 6,138,285 | A * | 10/2000 | Robrahn | A61F 9/028 2/434 |
| 6,276,795 | B1 * | 8/2001 | Hall | A61F 9/025 2/431 |
| 6,341,863 | B1 * | 1/2002 | Chen-Lieh | A63B 33/002 2/428 |
| 6,384,991 | B1 * | 5/2002 | Brown | A61F 9/029 359/813 |
| 6,427,254 | B1 * | 8/2002 | Gardner | A61F 9/02 2/444 |
| D477,010 | S * | 7/2003 | Moritz | D16/312 |
| 6,715,157 | B2 * | 4/2004 | Mage | A61F 9/029 2/426 |
| D515,615 | S * | 2/2006 | Fecteau | D16/312 |
| D537,098 | S * | 2/2007 | Sheldon | D16/311 |
| 7,175,275 | B2 * | 2/2007 | Ifergan | G02C 9/00 351/105 |
| 7,527,373 | B2 * | 5/2009 | Stanley | A61F 9/025 351/47 |
| 7,648,233 | B2 * | 1/2010 | Blanshay | G02C 9/00 351/136 |
| 7,654,666 | B2 * | 2/2010 | Stanley | G02C 3/003 2/452 |
| 7,686,447 | B2 * | 3/2010 | Stanley | A61F 9/025 351/47 |
| 7,725,959 | B2 | 6/2010 | Wang-Lee | |
| 8,065,752 | B2 * | 11/2011 | Kuroda | A63B 33/00 2/428 |
| 8,235,523 | B2 * | 8/2012 | Yang | A61F 9/025 2/429 |
| 8,286,271 | B2 * | 10/2012 | Chiang | A63B 33/002 2/448 |
| D675,249 | S * | 1/2013 | Giroux | D16/312 |
| D698,854 | S * | 2/2014 | McNeal | D16/312 |
| D700,929 | S * | 3/2014 | McNeal | D16/312 |
| D710,930 | S * | 8/2014 | McNeal | D16/312 |
| 2004/0117898 | A1 * | 6/2004 | Penque, Jr. | A61F 9/028 2/431 |
| 2007/0182916 | A1 * | 8/2007 | Blanshay | A61F 9/025 351/62 |
| 2008/0155736 | A1 * | 7/2008 | Paulson | G02C 9/04 2/441 |
| 2008/0172778 | A1 * | 7/2008 | Lysogorski | A42B 3/185 2/436 |
| 2008/0256688 | A1 * | 10/2008 | Bruce | A61F 9/025 2/441 |
| 2008/0301857 | A1 * | 12/2008 | Wang-Lee | A61F 9/025 2/431 |
| 2008/0301858 | A1 * | 12/2008 | Wang-Lee | A61F 9/025 2/436 |
| 2009/0268153 | A1 * | 10/2009 | Wang-Lee | A42B 3/185 351/155 |
| 2009/0300830 | A1 * | 12/2009 | Mage | A61F 9/025 2/441 |
| 2010/0064421 | A1 * | 3/2010 | Wang-Lee | A61F 9/025 2/428 |
| 2011/0083256 | A1 * | 4/2011 | Wang-Lee | A61F 9/025 2/434 |
| 2011/0219523 | A1 * | 9/2011 | Chiang | A63B 33/002 2/434 |
| 2011/0258759 | A1 * | 10/2011 | Renaud-Goud | A61F 9/026 2/428 |
| 2012/0180203 | A1 * | 7/2012 | Giroux | A61F 9/027 2/422 |
| 2013/0019387 | A1 * | 1/2013 | McNeal | A61F 9/028 2/436 |
| 2014/0043581 | A1 * | 2/2014 | Chen | G02C 9/04 351/57 |
| 2014/0115761 | A1 * | 5/2014 | McNeal | G02C 5/122 2/439 |

* cited by examiner

GOGGLE STRUCTURE

BACKGROUND OF THE INVENTION

1. Technical Field

The present invention relates to goggle structures and, more particularly, to a goggle structure with related components which can be inserted into each other by vertical engagement or by a predetermined segment thereof, such that not only are the related components of the goggle structure engaged with each other precisely when manipulated quickly, but the coupling portions of the related components also remain undamaged when dismounted.

2. Description of Related Art

Conventional eyeglasses have wide applications, including eyesight correction, sports, and preventing intense light from injuring the eye. The conventional eyeglasses are available in different categories for selection by users. The present invention is intended to improve the conventional sports eyeglasses. The conventional sports eyeglasses essentially comprise two integrally-formed lenses. The junction of the two integrally-formed lenses is coupled to a protective frame. The lateral sides of the two integrally-formed lenses are coupled to a cord disposed around the user's head comfortably. Hence, the conventional sports eyeglasses are safe and comfortable to wear.

U.S. Pat. No. 7,725,959 B1, entitled Protective Goggles and issued on Jun. 1, 2010, discloses a pair of protective goggles comprising: an integrally-formed lens, with an opening formed at a middle segment of an upper side of the lens for correspondingly engaging with an engaging portion on an upper side of the frame having a protective pad made of soft materials; and a protrusion extending upwardly from an inner surface of a nose supporting portion at a lower side of the lens to be correspondingly inserted into a hole adjacent to a concave segment formed on a middle segment of a lower side of the frame for positional restriction. The frame further has more than one rib extending on an upper side of the frame for correspondingly fitting with the lens and for stably propping the lens. A through hole is provided on each end of the frame and has a raised portion projected around the through hole. A tenon is formed adjacent to the raised portion and passing through an aperture of the lens, with the raised portion projecting through the corresponding through hole of the lens. A cord has two ends respectively combined with buckles for penetration and change in direction, such that the cord is fastened integrally to the buckles.

The present invention provides, a novel design based on the configuration of related components of a goggle structure which falls within the same category as the aforesaid protective goggles. The goggle structure comprises related components, such as a protective soft pad, a frame, and a subsidiary lens frame, which can be inserted into each other by vertical engagement or by a predetermined segment thereof. Thus, not only are the related components of the goggle structure engaged with each other precisely when manipulated quickly, but the coupling portions of the related components also remain undamaged when dismounted.

BRIEF SUMMARY OF THE INVENTION

The present invention provides a novel goggle structure based on the configuration of components of conventional protective goggles. The goggle structure comprises a protective soft pad, a frame, and a subsidiary lens frame and is characterized in that the subsidiary lens frame and the frame are capable of corresponding positional insertion, and the frame is received in a receiving space disposed at the protective soft pad. Hook portions formed on upper and lower sides of the frame and extending backward press against adjacent peripheries of the receiving space. Pressing portions formed on an upper portion at the middle segment of the frame allow the protective soft pad to be pushed and inserted into the pressing portions. Carrying portions formed on a lower portion at the middle segment of the frame can be straddled by the bottom portion of the subsidiary lens frame easily. Branch portions extend from two outer sides of the frame and can be inserted into a concave portion of the protective soft pad. Therefore, related components of the goggle structure are engaged with each other precisely.

It is an objective of the present invention to provide a goggle structure comprising a protective soft pad, a frame, and a subsidiary lens frame. Convex portions are formed bilaterally on upper and lower sides of the subsidiary lens frame and inserted into slots disposed at the frame, respectively. Hook portions are formed on upper and lower sides of the frame and extend backward, such that the frame is received in the receiving space disposed at the protective soft pad to allow the hook portions to press against adjacent peripheries of the receiving space. The pressing portions and the carrying portions are formed on upper and lower portions at the middle segment of the frame. A forward-facing opening is disposed concavely on the protective soft pad and can be pushed and inserted into the pressing portions. The bottom portion of the subsidiary lens frame straddles the carrying portions. Branch portions extend from two outer sides of the frame and can be inserted into a concave portion of the protective soft pad. Hence, related components are engaged with each other.

Another objective of the present invention is to provide the goggle structure characterized in that the hook portions disposed at ends of the frame and received in the receiving space circumferentially disposed at the protective soft pad bend to form a pressing edge, such that the hook portions of the frame press firmly against the periphery of the receiving space.

Yet another objective of the present invention is to provide the goggle structure characterized in that the hook portions disposed at ends of the frame and received in the receiving space circumferentially disposed at the protective soft pad bend vertically to form a T-shaped pressing edge facing sideward, such that the hook portions of the frame press against the periphery of the receiving space to hold the frame firmly from above and below.

DETAILED DESCRIPTION OF THE INVENTION

Figure 1:
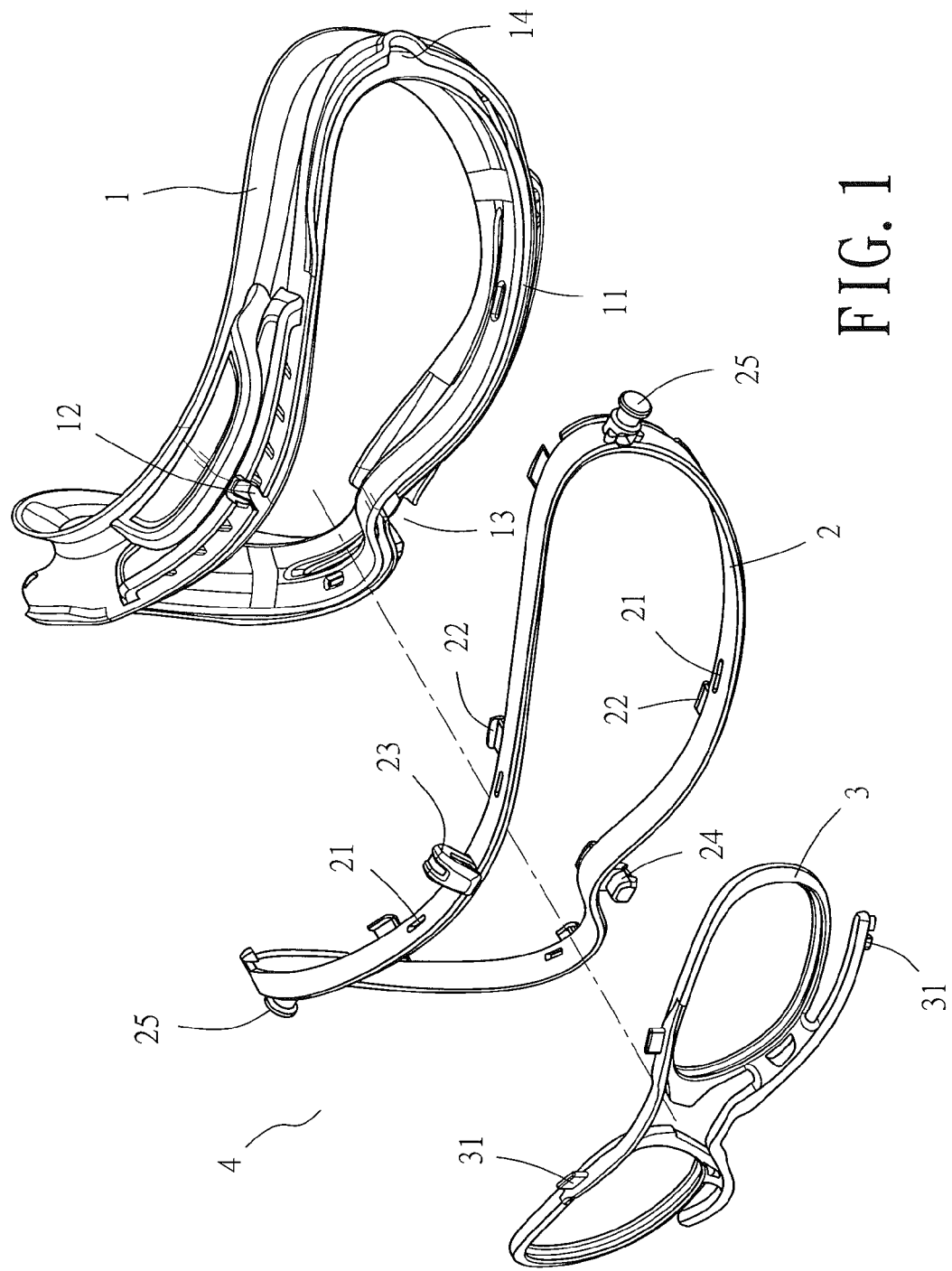
FIG. 1 is an exploded view of a goggle structure according to the present invention.

The present invention provides a goggle structure. Referring to FIG. 1, a goggle 4 comprises a protective soft pad 1, a frame 2, and a subsidiary lens frame 3.

Figure 2:
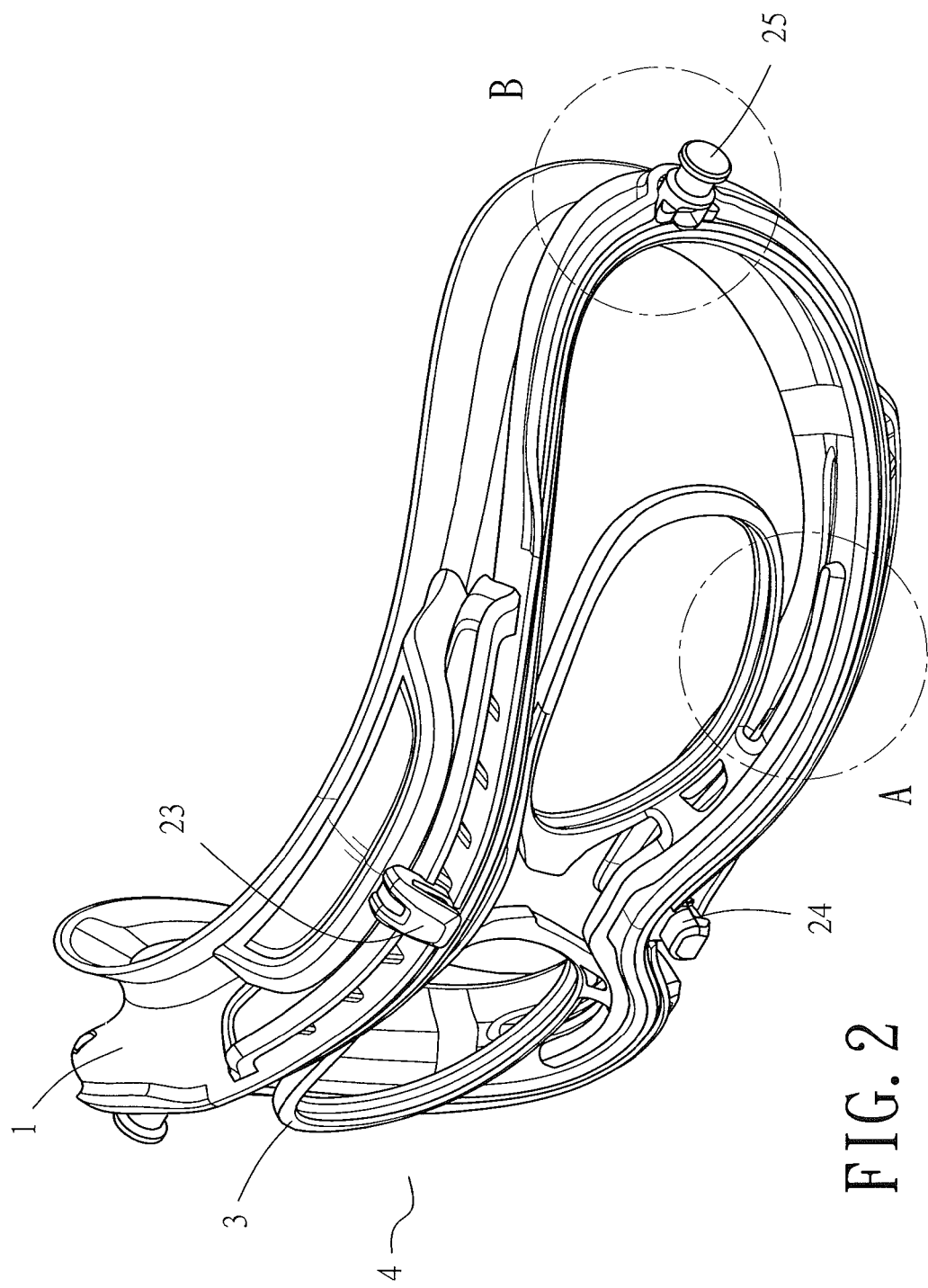
FIG. 2 is a perspective view of the goggle structure according to the present invention.
Figure 2B:
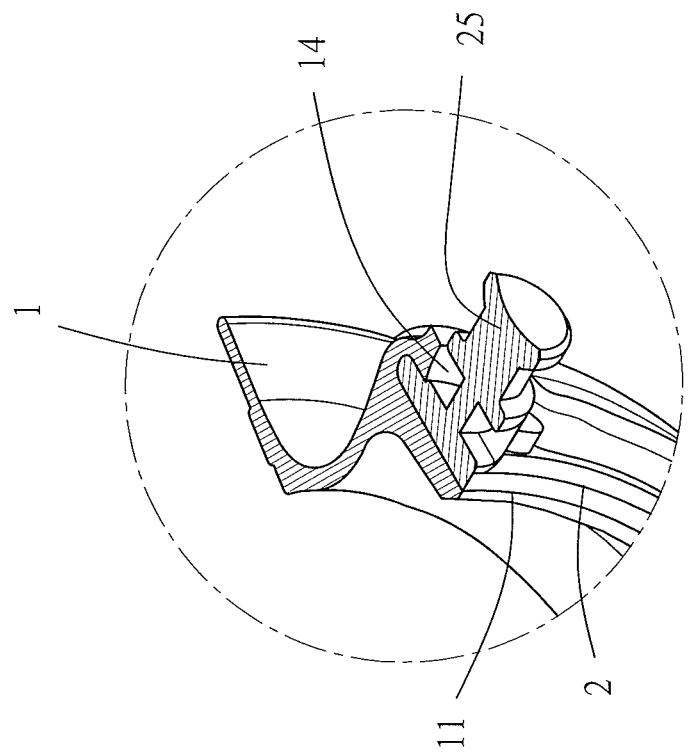
FIG. 2B is a cross-sectional view of portion B in FIG. 2.
Figure 2A:
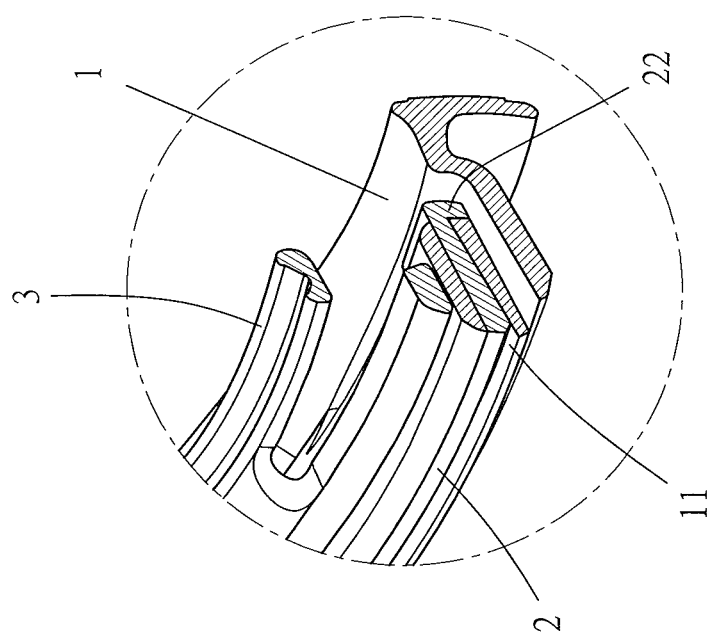
FIG. 2A is a cross-sectional view of portion A in FIG. 2.

A receiving space 11 is circumferentially disposed at the periphery of the protective soft pad 1 as shown in FIG. 2A. Forward-facing openings 12, 13 are disposed concavely on the protective soft pad 1 and positioned proximate to the outer periphery of the receiving space 11, and correspond in position to the upper and lower portions thereof. A concave portion 14 opening outward is disposed on the protective soft pad 1 and corresponds in position to the two sides of the receiving space 11.

Parts and components appropriately connectable to the frame 2 are selected according to the receiving space 11 circumferentially disposed at the periphery of the protective soft pad 1. At least a slot 21 is disposed on the upper and lower sides of the frame 2. At least a hook portion 22 is formed on the upper and lower sides of the frame 2 and extends backward (the hook portions 22 bend to form an L-shaped pressing edge facing sideward), such that the hook portions 22 of the frame 2 press firmly against the periphery of the receiving space 11. Pressing portions 23 and carrying portions 24 are formed on the upper and lower portions at the middle segment of the frame 2. Branch portions 25 extend from two outer sides of the frame 2.

A second functional lens is admitted into and coupled to the subsidiary lens frame 3, as the subsidiary lens frame 3 is provided in the form of a predetermined single frame or left and right self-contained frames selected according to the internal configuration of the frame 2. Convex portions 31 are formed on the upper and lower sides of the subsidiary lens frame 3.

Figure 3:
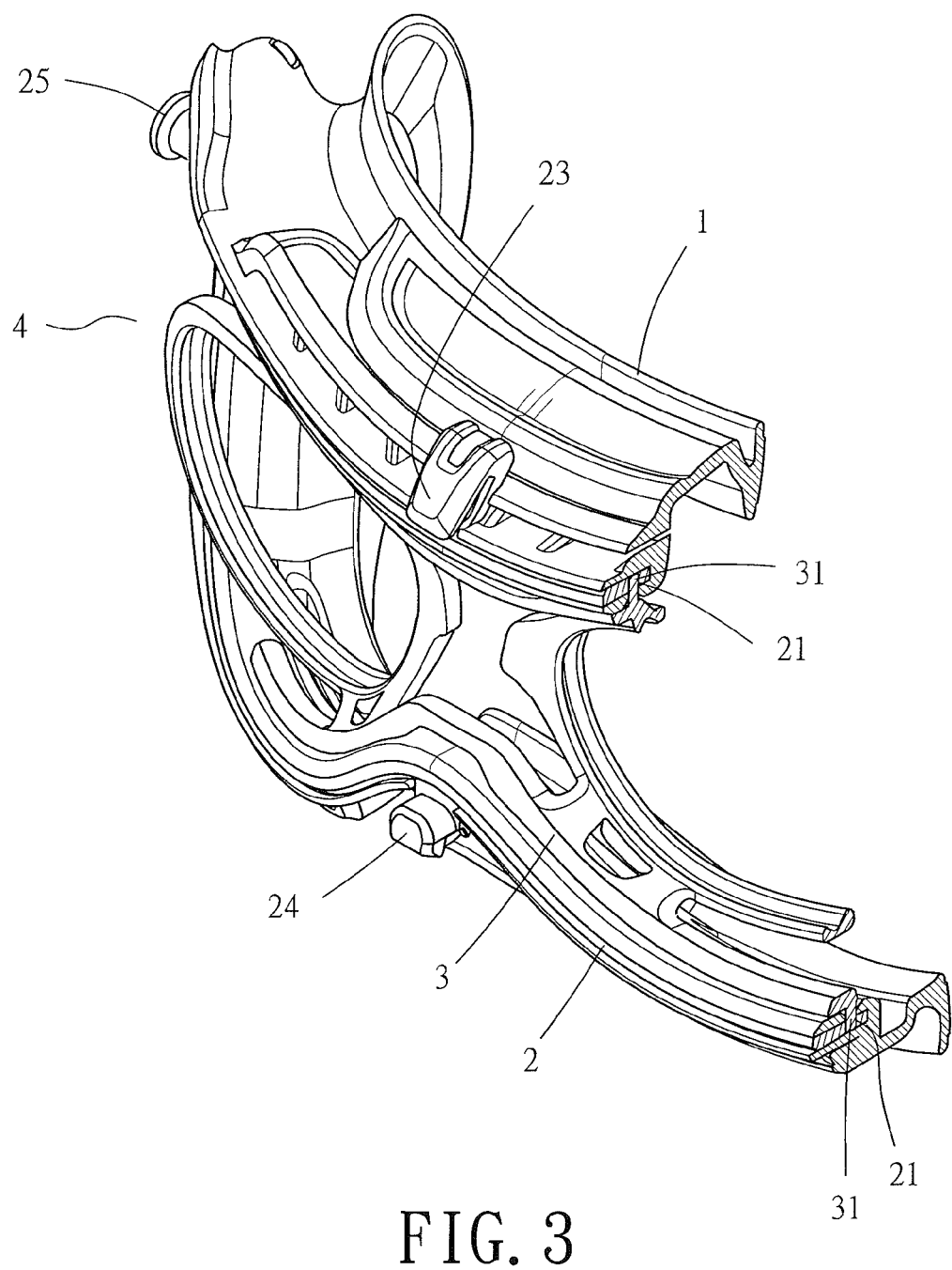
FIG. 3 is an outward longitudinal cross-sectional view of the goggle structure according to the present invention.
Figure 4:
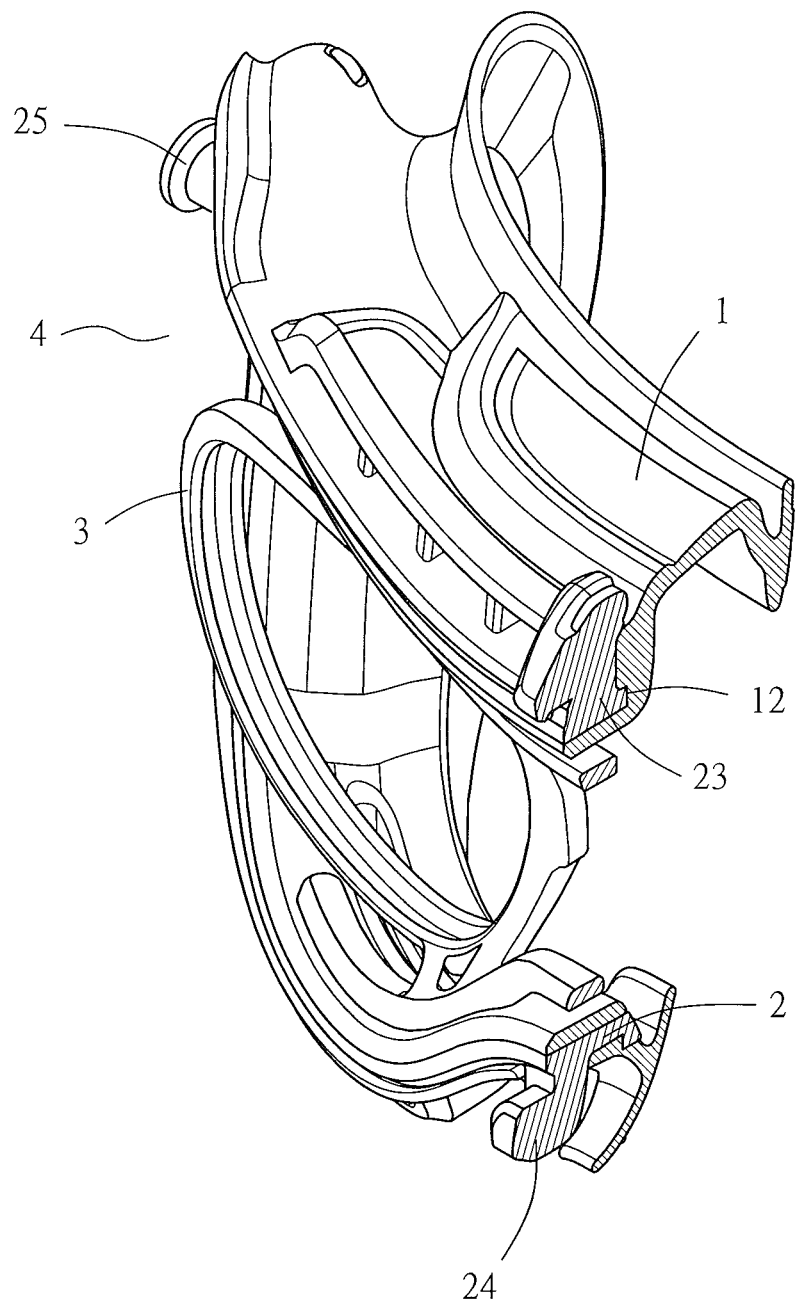
FIG. 4 is a longitudinal cross-sectional view of a middle segment of the goggle structure according to the present invention.

The protective soft pad 1, the frame 2, and the subsidiary lens frame 3 are put together by following three steps of a process flow illustrated with FIG. 1 and FIG. 2 and described below. The first step involves inserting the convex portions 31 formed on the upper and lower sides of the subsidiary lens frame 3 into slots 21 disposed at the frame 2, respectively. The second step involves inserting the frame 2 into the receiving space 11 circumferentially disposed at the protective soft pad 1 as shown in FIG. 3, such that each of the hook portions 22 formed on the upper and lower sides of the frame 2 and extending backward presses against adjacent peripheries of the receiving space 11 as shown in FIG. 2A. The opening 12 opening forward and disposed concavely on the protective soft pad 1 can be pushed and inserted into the pressing portions 23 of the frame 2, such that the bottom portion of the subsidiary lens frame 3 straddles the carrying portions 24 of the frame 2 as shown in FIG. 4. In the third step, the branch portions 25 extend from two outer sides of the frame 2 to press against the concave portion 14 disposed at the protective soft pad 1 as shown in FIG. 2B, such that related components of the goggle structure are engaged with each other precisely.

Figure 5:
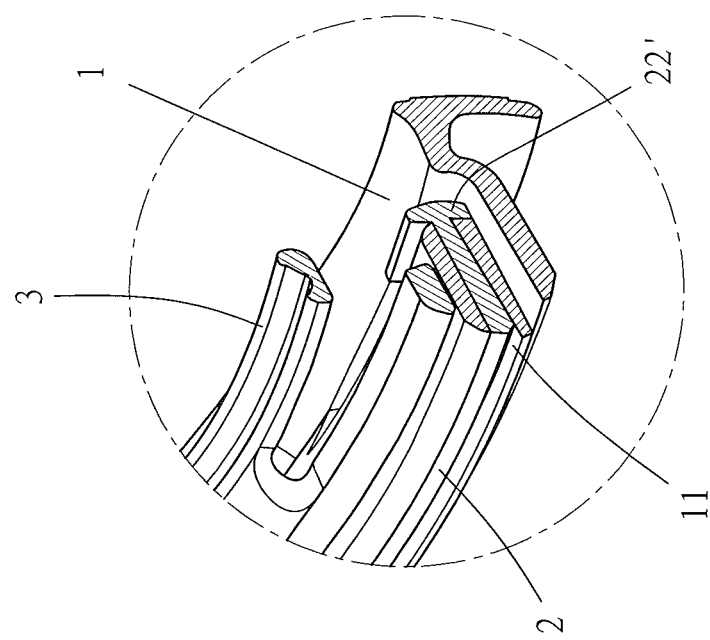
FIG. 5 is a cross-sectional view of a frame, a subsidiary lens frame, and a protective soft pad according to another embodiment of the present invention.

Hook portions 22', which are disposed at the ends of the frame 2 received in the receiving space 11 circumferentially disposed at the protective soft pad 1, bend vertically to form a T-shaped pressing edge facing sideward as shown in FIG. 5, such that the hook portions 22' of the frame 2 press against the periphery of the receiving space 11 to hold the frame 2 firmly from above and below.

What is claimed is:

1. A goggle structure comprising a protective soft pad, a frame, and a subsidiary lens frame, wherein convex portions are formed on upper and lower sides of the subsidiary lens frame and inserted into slots disposed at the frame, respectively, wherein hook portions are formed on upper and lower sides of the frame and extend backward, wherein the frame is received in a receiving space circumferentially disposed at the protective soft pad to allow the hook portions to press against adjacent peripheries of the receiving space, wherein pressing portions and carrying portions are formed on upper and lower portions at a middle segment of the frame, wherein a forward-facing opening disposed concavely on the protective soft pad is pushed and inserted into the pressing portions, wherein a bottom portion of the subsidiary lens frame straddles the carrying portions, wherein branch portions extending from two outer sides of the frame press against a concave portion disposed at the protective soft pad and positioned proximate to the receiving space such that related components of the goggle structure are engaged with each other.

2. The goggle structure of claim 1, wherein the hook portions are disposed at ends of the upper and lower sides of the frame and received in the receiving space circumferentially disposed at the protective soft pad and bend to form a pressing edge, and wherein the hook portions of the frame press firmly against a periphery of the receiving space.

3. The goggle structure of claim 1, wherein the hook portions are disposed at ends of the upper and lower sides of the frame and received in the receiving space circumferentially disposed at the protective soft pad and bend vertically to form a T-shaped pressing edge, wherein a base of the T-shaped pressing edge extends rearward from the ends of the upper and lower sides of the frame, and wherein the hook portions of the frame press against a periphery of the receiving space to hold the frame firmly.

* * * * *